(12) United States Patent
Geiger et al.

(10) Patent No.: US 10,456,495 B2
(45) Date of Patent: Oct. 29, 2019

(54) PACKAGING DEVICE FOR MEDICAL PRODUCTS TO BE STERILIZED OR HAVING BEEN STERILIZED COMPRISING INTERNAL FIXATION

(71) Applicant: B. BRAUN MELSUNGEN AG, Melsungen (DE)

(72) Inventors: Ralph Geiger, Felsberg (DE); Peter Van Venrooy-Markefka, Berlin (DE)

(73) Assignee: B. Braun Melsungen AG (DE)

( * ) Notice: Subject to any disclaimer, the term of this patent is extended or adjusted under 35 U.S.C. 154(b) by 145 days.

(21) Appl. No.: 15/613,651

(22) Filed: Jun. 5, 2017

(65) Prior Publication Data

US 2017/0348451 A1 Dec. 7, 2017

(30) Foreign Application Priority Data

Jun. 7, 2016 (DE) ........................ 10 2016 110 486

(51) Int. Cl.
| | | |
|---|---|---|
| *B65D 75/56* | (2006.01) | |
| *A61L 2/26* | (2006.01) | |
| *B65D 75/04* | (2006.01) | |
| *B65D 77/04* | (2006.01) | |

(Continued)

(52) U.S. Cl.
CPC ............ *A61L 2/26* (2013.01); *A61B 1/00144* (2013.01); *A61B 50/00* (2016.02); *A61B 50/20* (2016.02);
(Continued)

(58) Field of Classification Search
CPC ........ B65D 75/04; B65D 75/56; B65D 77/04; B65D 81/2023; A61L 2/26;
(Continued)

(56) References Cited

U.S. PATENT DOCUMENTS

| | | | | |
|---|---|---|---|---|
| 5,009,515 A | * | 4/1991 | Bennett ................ | B65D 33/246 206/806 |
| 5,549,388 A | * | 8/1996 | Wilkes ................... | B65D 33/20 206/438 |

(Continued)

FOREIGN PATENT DOCUMENTS

| | | |
|---|---|---|
| DE | 102006027304 A1 | 12/2007 |
| DE | 69938259 T2 | 2/2009 |
| WO | 2011070329 A1 | 6/2011 |

OTHER PUBLICATIONS

Extended European Search Report for European Application No. 17173922.0, dated Oct. 20, 2017, including English language translation, 12 pages.

(Continued)

*Primary Examiner* — Luan K Bui
(74) *Attorney, Agent, or Firm* — RatnerPrestia

(57) ABSTRACT

A packaging device including a receiving compartment for medical products to be sterilized or having been sterilized, the receiving compartment being sealable in a sterile manner; a carrier for hanging and/or guiding and/or handling the packaging device, wherein the carrier extends into the interior of the receiving compartment and includes at least one accurately fitting mount for a section of a medical product to be sterilized or having been sterilized. Also, secondary packaging for accommodating a plurality of such packaging devices.

14 Claims, 4 Drawing Sheets

(51) Int. Cl.
*B65D 81/20* (2006.01)
*A61B 50/00* (2016.01)
*A61B 50/20* (2016.01)
*A61B 50/22* (2016.01)
*A61B 50/31* (2016.01)
*A61B 50/28* (2016.01)
*A61B 1/00* (2006.01)
*A61B 50/30* (2016.01)

(52) U.S. Cl.
CPC .............. *A61B 50/22* (2016.02); *A61B 50/28* (2016.02); *A61B 50/31* (2016.02); *B65D 75/04* (2013.01); *B65D 75/56* (2013.01); *B65D 77/04* (2013.01); *B65D 81/2023* (2013.01); *A61B 2050/3011* (2016.02); *A61B 2050/311* (2016.02); *A61L 2202/24* (2013.01)

(58) Field of Classification Search
CPC ....... A61L 2202/24; A61B 1/00; A61B 50/00; A61B 50/20; A61B 50/22; A61B 50/28; A61B 50/31; A61B 2050/3011; A61B 2050/311
USPC .......... 383/23; 206/278, 279, 284–289, 363, 206/368, 369, 438, 461, 466, 495, 806
See application file for complete search history.

(56) References Cited

U.S. PATENT DOCUMENTS

| | | | | |
|---|---|---|---|---|
| 6,419,088 | B1* | 7/2002 | Barrois | B65D 25/107 206/438 |
| 6,594,971 | B1* | 7/2003 | Addy | A61B 1/00142 53/413 |
| 7,631,760 | B2* | 12/2009 | Guelzow | A61F 2/0095 206/204 |
| 2003/0188981 | A1* | 10/2003 | Sedley | A61L 2/26 206/363 |
| 2006/0260967 | A1* | 11/2006 | Clarke | A61F 2/0095 206/438 |
| 2009/0236253 | A1 | 9/2009 | Merckle et al. | |
| 2016/0193073 | A1* | 7/2016 | Kinsey | A61F 5/4408 604/328 |

OTHER PUBLICATIONS

German Search Report for German Application No. 10 2016 110 486.8, dated Jan. 5, 2017 with translation, 14 Pages.

* cited by examiner

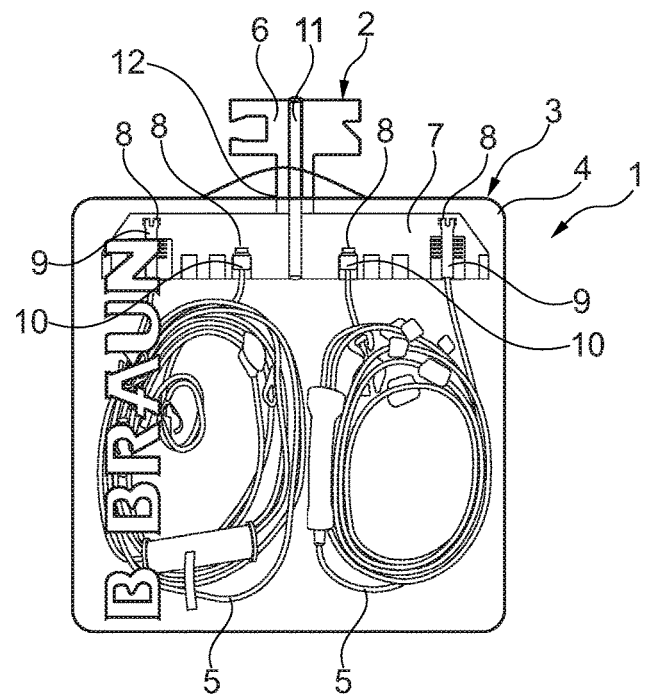
Fig. 1
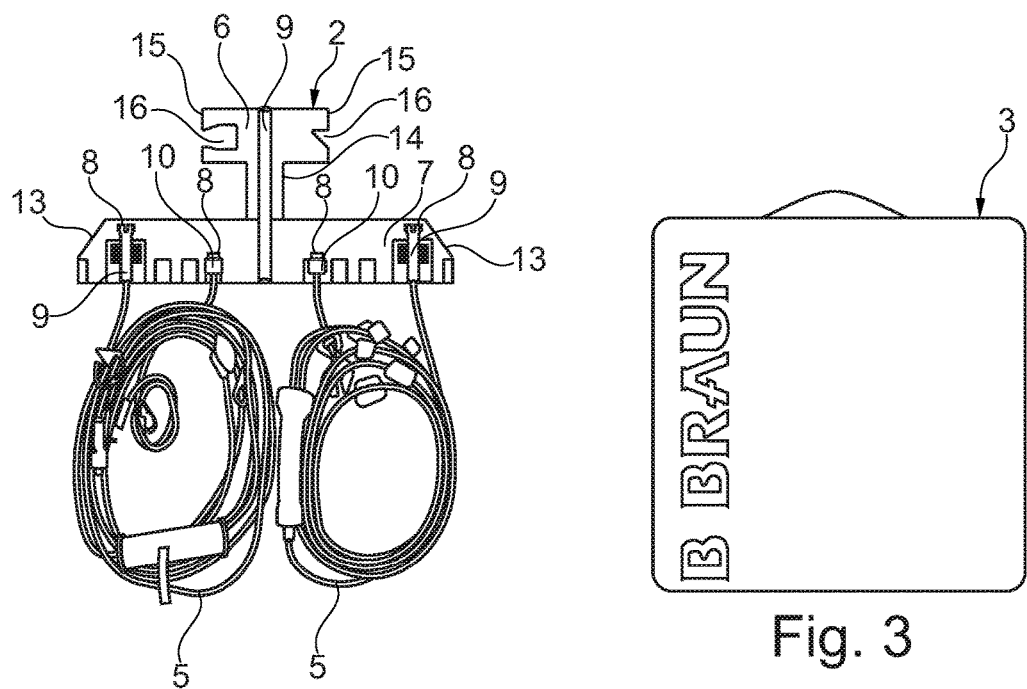
Fig. 2
Fig. 3

PACKAGING DEVICE FOR MEDICAL PRODUCTS TO BE STERILIZED OR HAVING BEEN STERILIZED COMPRISING INTERNAL FIXATION

CROSS REFERENCE TO RELATED APPLICATIONS

This application claims priority to German application DE 10 2016 110 486.8 filed Jun. 7, 2016, the contents of such application being incorporated by reference herein.

FIELD OF THE INVENTION

The invention relates to a packaging device comprising a receiving compartment for medical products which are to be sterilized or have been sterilized, the receiving compartment being closable in a sterile manner; and a carrier for hanging and/or guiding and/or handling the packaging device. Moreover, the invention relates to a secondary packaging for accommodating a plurality of such packaging devices.

BACKGROUND OF THE INVENTION

Medical products such as tube systems, catheters or intravenous sets are basically packed in sterile packages, sterilized within the latter and subsequently delivered. A sterile package on the one hand has to allow for sterilization and, on the other hand, has to ensure the sterility during appropriate storage until use of the medical products received therein. In general, re-contamination of the sterilized medical product after preparation thereof until use thereof has to be excluded. Medical single-use products such as blood tubes or surgical instruments are packed in bags or blister packs and are subsequently sterilized in a way known from prior art. The sterilization may be carried out in an individual package, in a dispenser box or stacked on a pallet. In the packages known from prior art the products are basically arranged loosely, i.e. not fixed within the (primary) package/a bag/a blister pack.

The loose arrangement of the medical products to be sterilized or having been sterilized in the package has the drawback, however, that during handling and transportation the packaged medical products are damaged or impaired especially by deformations, kinks or damage of the package. Moreover, the loose arrangement of the medical products in a bag may entail contamination, when plural loosely packed products such as blood tubes are removed, as at least portions of the products may get in contact with the ground during removal.

Furthermore, for example during electron beam sterilization (so called E-beam technology) the loose arrangement within the package results in an uneven distribution of the dose due to high scattered radiation which results in non-homogenous load of the medical products. The electron beam sterilization is based on penetration of the medical products to be sterilized including the package by highly energetic accelerated electrons which have an ionizing effect and thus are germ-killing. If in electron beam sterilization a required minimum radiation is gone below due to the scattered radiation, this results in non-sterility. On the other hand, over-radiation in the form of excessive energetic load of the medical products to be sterilized results in material changes such as discoloring, deterioration of the mechanical properties or ageing. Thus, the loose arrangement of the medical products to be sterilized does not allow, in the case of beam sterilization, minimized radiation of the individual medical product. Due to the high scattering occurring, an output of the beam source has to be high so as to ensure minimum radiation and thus sterility. An optional gas sterilization, on the other hand, produces high residual gas values and additionally requires a gas-permeable package.

Further drawbacks of prior art reside in the fact that the package after sterilization has to be further provided with a label for marking during an additional production step and that automated manufacture and, respectively, packaging of the medical products is possible to a limited extent only.

SUMMARY OF THE INVENTION

Hence it is an object of the invention to avoid or at least alleviate the drawbacks of prior art. Especially a packaging device avoiding loose arrangement and accompanying slipping of medical products within the same is to be provided. The packaging device is especially intended to optimize processing during sterilization and to improve durability, stability and labeling of the package. Moreover, transportation of a plurality of such packaging devices is to be optimized.

These objects are achieved especially by a packaging device according to the features of the independent claim as well as by a secondary packaging as defined by the claims. Advantageous further developments are the subject matter of the subclaims.

First of all, the invention relates to a packaging device comprising a receiving compartment for medical products which are to be sterilized or have been sterilized, the receiving compartment being sealable/closable in a sterile manner; and a carrier for hanging/suspending and/or guiding and/or handling the packaging device, wherein the carrier extends into the interior of the receiving compartment and includes at least one preferably accurately/exactly fitting mount/seating for a section of a medical product to be sterilized or having been sterilized.

Accordingly, the receiving compartment is understood to be a volume sealed/closed in a sterile manner in which the sterilized or to be sterilized medical products are located. According to aspects of the invention, the carrier is provided outside and inside the receiving compartment and outside the receiving compartment serves for hanging/suspending, guiding, handling and appropriately precisely orientating the packaging device/the package and inside the receiving compartment serves for fixing the medical products to be sterilized or having been sterilized and for avoiding pressure marks on the package.

Such packaging device helps to achieve that the medical products to be sterilized or having been sterilized are no longer present loosely in the package and, respectively, in the receiving compartment, but are accommodated/fixed/secured on a carrier inside the receiving compartment and, respectively, inside the package. This allows positioning and, respectively, arranging the medical products at a predetermined position so that a defined position can be obtained inside the packaging device. Furthermore, a repeatable arrangement and, respectively, positioning of the medical products is facilitated and slipping of the latter is minimized or excluded.

Thus, according to aspects of the invention, the aforedescribed drawbacks of a loose arrangement of the medical products within the package are avoided. Especially, such packaging device results in more suitable transportation, enhanced handling, orientation, labeling and automation. Furthermore, the packaging device according to aspects of the invention is better adapted to the requirements to a packaging device in beam sterilization, especially electron beam sterilization. By fixation on the carrier, in addition possible contamination of the medical products during removal of the same is counteracted.

Accordingly, it is useful when the carrier/carrier system includes an external guiding portion which is especially configured for hanging/suspending and/or guiding and/or handling the packaging device and an internal receiving portion which is especially configured for receiving the medical product to be sterilized or having been sterilized in an accurately fitting manner, wherein the external guiding portion is disposed outside the receiving compartment and the internal receiving portion is disposed inside the receiving compartment and the internal receiving portion and the external guiding portion are formed integrally, preferably made from one material, especially as a plastic part manufactured by injection molding.

Consequently, by the carrier according to aspects of the invention functions and technical effects inside and outside the receiving compartment are realized. The carrier comprising the external guiding portion and the internal receiving portion is an integral component preferably made from one material and thus can be easily and inexpensively manufactured by injection molding. The carrier comprises a sufficiently beam-resistant as well as stiff and strong plastic material and may include markings, especially laser markings which may contain user instructions.

It is further advantageous when the receiving compartment is configured by a film package, especially in the manner of a film bag having a tab for closing the film bag, wherein at an interface where the carrier is transformed into the interior of the film package an adhesive/bonded connection, especially by welding or gluing, is formed between the carrier and the film package. In this way, the adhesive connection at the interface between the carrier and the film package helps to obtain sterile sealing of the receiving compartment. This offers the advantage that re-contamination after sterilization is quasi excluded.

In other words, the packaging device or primary packaging thus is made of a carrier/carrier system and a film package/film bag, wherein the especially pliable film package/film bag in its interior forms the receiving compartment of the present invention. In accordance with the invention, the film package/film bag comprises sufficiently beam-resistant and/or pressure-resistant plastic material. It may be freely designed and may be pre-printed, for example, and/or may include an UDI (Unique Device Identification) and/or an IFU (Instruction for Use). The film package closes the mount/seating provided on the carrier. The film package may also be glued or laminated onto the carrier and/or may be configured to be closely adjacent to the carrier so that the fixation according to aspects of the invention of the medical products to be sterilized or having been sterilized may additionally be performed also by the film package.

One advantageous embodiment is wherein the carrier includes an evacuating means, especially in the fashion of a vacuum channel, through which at least a partial vacuum, preferably a vacuum, can be produced in the receiving compartment. In this way, air enclosed in the receiving compartment/inside the film package/film bag can be removed or sucked from the receiving compartment. Initially this offers the advantage that the medical products arranged in the receiving compartment are additionally secured and, respectively, fixed by the partial vacuum or the vacuum. Moreover, the packaging volume is largely reduced by the partial vacuum or the vacuum.

Due to enclosed air, in beam sterilization frequently ozone is formed inside the package, which may damage the packed products or may entail an ozone load of the user, so that this drawback can be eliminated by applying (partial) vacuum. Hence providing an evacuating means offers advantages, when the medical products are fixed, as regards the packaging volume and during beam sterilization. It is understood that the evacuating means has to include a sealing option in the form of a sealing device so that the receiving compartment continues to be sealable in a sterile manner.

Moreover, it is of advantage when the external guiding portion is in the form of a guide hook, especially in the manner of a hanger hook or T-shaped having two lateral recesses, for suitable orientation and/or handling and/or guiding of the packaging device. The carrier thus may include a T-shaped guide hook having two lateral recesses by which the guide hook can be clipped or engaged in one or two guide rails, for example. Alternatively, the carrier may have a hanger-type guide hook which can be suspended at a guide rail, for example. The packaging device thus can be suspended or arranged e.g. on a guide rail. Accordingly, the evacuating device/the vacuum channel according to aspects of the invention may be provided in the guide hook.

The guide hook enables appropriate guiding both during production or manufacture and during sterilization, suitable orientation as well as automated handling of the packaging device. Thus, with the carrier and, respectively, the guide hook a suspended or guided transportation and precise supply to a sterilization unit are obtained. The carrier and, respectively, the guide hook thus enable the sterilization process to be automated and a material flow to be enhanced, especially by possibly providing a buffer accompanied by avoiding stop times. The guide hook is located outside the receiving compartment and thus constitutes a non-sterile section of the carrier or the carrier structure, respectively.

The guide hook may include marks in the form of laser markings, color codes etc. or labels arranged thereon which contain user instructions. Said instructions may be such that, when taking the arranged marks, codes, markings or labels into account, a user virtually cannot make any errors so that in the guide hook an error prevention unit/error prevention system may be provided.

One advantageous embodiment is wherein the at least one mount/seating for a section of a medical product to be sterilized or having been sterilized is formed in the manner of a connector which receives, orientates and fixes the medical products to be sterilized or having been sterilized in the receiving compartment, the connector comprising an especially U-shaped recess for positively mounting/locking/form fitting, especially clipping or engaging, the medical products to be sterilized or having been sterilized. Thus, inside the receiving compartment and, respectively, the film package/film bag the carrier comprises connector sections or connector clips into which sections of the medical products to be sterilized of having been sterilized can be clipped or engaged. According to aspects of the invention, also automated clipping or engaging is imaginable. The connector sections may be in the form of Luer lock connectors, Hansen connectors or small-bore connectors, for example.

The medical products thus are positively secured/form fitted to the carrier by clipping or engaging so that simple securing/simple attaching as well as simple removal of the medical products are facilitated. The connector sections enable the medical products to be fixed to the carrier and to be precisely orientated during sterilization. The connector sections can be configured so that sections of medical products can be received therein with accurate fit. For example, the connector sections may be configured as accurately fitting recesses. Also, the mounts and, respectively, connector sections on a carrier may differ as to their shape and configuration so that each mount and, respectively, each connector may be formed to be accurately fitting to the section of the medical product to be received therein. Hence, a mount of the medical products suited for the application is provided on the carrier. The fixation moreover prevents ground contact during removal.

It is useful when the at least one mount/seating for a section of a medical product to be sterilized or having been sterilized includes a marking and/or the mount is adapted as to its shape and/or configuration to the section of the medical product to be sterilized or having been sterilized which is received therein. In this way, a user is able to know from a marking such as a color marking or from the shape and/or the configuration of the mount which medical products and, respectively, which section of the medical product has to be arranged and, respectively, fixed in the specific mount.

For example, in a case in which two tubes, i.e. a blood line and a flush line, are provided in the package, red marks may be arranged for the blood line and blue marks may be arranged for the flush line so that a user actually cannot confuse the blood line ports with the flush line ports when removing the tubes. Possible marks basically are colors, shapes, words etc. This offers the advantage that errors of a user during fixation, removal and application can be prevented. Thus an error prevention unit is provided also inside the receiving compartment on the carrier.

Advantageously, inside the receiving compartment the carrier further comprises at least two, preferably three or four, stacking portions/stacking clips spanning the receiving compartment for appropriately stacking and/or guiding the packaging device. This has the effect that inside the receiving compartment there are provided sections which allow for facilitated stacking or stacking capability of the packaging device. On the one hand, this offers the advantage of reduced mechanical load and thus improved storage of a plurality of packaging devices according to aspects of the invention in a secondary package such as a cardboard box or receptacle. On the other hand, for example during sterilization appropriate guiding and orientation of the packaging device are enabled. Moreover, the stacking sections help to prevent pressure marks on the package.

It is moreover advantageous when inside the receiving compartment the carrier is configured to be U-shaped or horseshoe-shaped for lateral protection of the medical products to be sterilized or having been sterilized which are received in the receiving compartment. Such design of the carrier largely enhances the stability of the packaging device, the medical products are protected and thus durability of the packaging device is improved. Moreover, such design of the carrier may help to prevent pressure marks.

In other words, the invention first relates to a package comprising a carrier system for internal fixation of packaged products, especially medical products. A loose arrangement of medical products in a sterile package is detrimental in various respects. The drawbacks of prior art are eliminated by fixing the medical products inside the package according to aspects of the invention. Especially, a carrier system enables direct sterilization of an individual package by beam sterilization, in particular by electron beam sterilization (so called E-beam technology). The optimized packaging of the present invention permits reduced radiation time, less scattered radiation as well as smaller energetic load. The packaging device of the present invention thus is adapted especially to the requirements of E-beam technology; however, as afore-mentioned, the fixation also offers advantages for medical products sterilized in a different way.

The invention further relates to a secondary packaging for receiving a plurality of packaging devices according to aspects of the invention, the secondary packaging being in the form of a receptacle and including a guide rail on which the carriers of the packaging devices can be arranged. Thus appropriate arrangement, fixed orientation, easy removal, small mechanical load, especially during transportation, and automated packaging of the packaging devices according to aspects of the invention in a secondary packaging are achieved. This offers the advantage that the number of remaining packaging devices including the medical products received therein is immediately visible at any time. This is not the case with loose packages which are randomly located in a secondary packaging.

It is useful when a height and a width of the secondary packaging and, respectively, of the receptacle are formed corresponding to the outer dimensions of the packaging device according to aspects of the invention. In this way, the volume of the secondary packaging can be largely reduced.

According to aspects of the invention, also transportation of the packaging devices accommodated in the secondary packaging is considerably improved.

BRIEF DESCRIPTION OF THE DRAWINGS

The invention is best understood from the following detailed description when read in connection with the accompanying drawings. Included in the drawings are the following figures:

FIG. 1 shows a front view of a first embodiment of the packaging device according to aspects of the invention;

FIG. 2 shows a front view of a carrier of the first embodiment of the packaging device according to aspects of the invention including medical tubes received thereon;

FIG. 3 shows a front view of a film bag according to aspects of the invention—forming a receiving compartment;

The Figures are merely schematic and merely serve for the comprehension of the invention. Like elements are provided with like reference numerals. The features of the individual embodiments may be exchanged for each other.

DETAILED DESCRIPTION OF THE PREFERRED EMBODIMENTS

Figure 4:
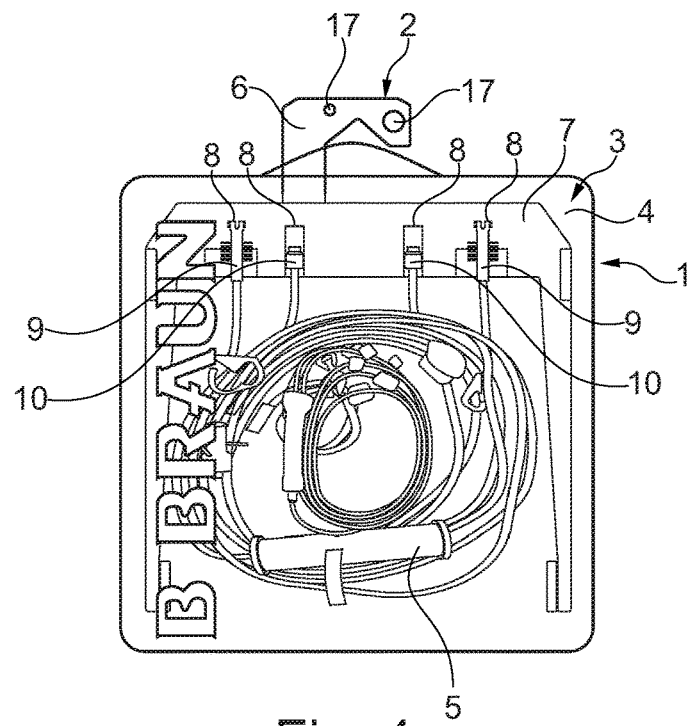
FIG. 4 shows a front view of a second embodiment of the packaging device according to aspects of the invention.

FIG. 1 shows a front view of a first embodiment of the sterile package/packaging 1 according to aspects of the invention. The sterile package 1 includes a carrier 2 and a film bag 3. Inside the film bag 3, i.e. in a package interior 4, two wound medical tubes 5 are located. The carrier is formed outside the film bag 3 as a T-shaped guide hook 6 and extends into the package interior 4. In the package interior 4 the carrier 2 includes a receiving section 7 having four mounts/seatings 8, wherein a starting connector plug 9 (having a Luer lock) and an end connector plug 10 (having a Luer lock) of the first medical tube 5 (blood tube system for hemodialysis) as well as a starting connector plug 9 and an end connector plug 10 (each equally having a Luer lock) of the second medical tube 5 are clipped in said mounts. The mounts 8 differ from each other and are formed to be accurately fitting to the starting connector plug 9 and, respectively, the end connector plug 10. The receiving section 7 is arranged at an upper portion of the film bag 3. The winding of the medical tubes 5 and the clipping of the starting connector plugs 9 and the end connector plugs 10 of the tubes 5 into the mounts 8 ensure safe fixation of the two tubes 5. The carrier 2 further includes a vacuum channel 11 which extends from outside into the package interior 4. The film bag 3 is closed by a tab (not shown). At an interface 12 the carrier 2 and the film bag 3 are bonded/adhesively connected to each other.

In FIG. 2 a front view of the carrier 2 of the first embodiment of the sterile package 1 according to aspects of the invention comprising medical tubes 5 received thereon is shown. The tubes 5 are wound and the starting connector plugs 9 as well as the end connector plugs 10 of the tubes 5 are clipped into the four mounts 8. Clipping can be performed freely from the top, from the front, from the bottom or from the side. The receiving section 7 of the carrier 2 in the package interior 4 is approximately rectangular in the front view, but has respective bevels/chambers 13 at the two upper corners in FIG. 2 which coincide with corners of the film bag 3. The bevels 13 prevent the film bag 3 from being damaged by pointed corners. The length of the receiving section 7 approximately corresponds to the length of the upper edge of the film bag 3 in the front view. The width of the receiving section 7 is small as compared to the length. The T-shaped guide hook 6 extends outwards and, respectively, upwards away from a center of the receiving section 7. The guide hook 6 comprises a neck portion 14 which is arranged perpendicularly to the receiving section 7 and two guide rail receiving sections 15 which are formed by lateral recesses 16 in the guide hook 6. The neck portion 14 and the guide rail receiving portions 15 together form the T-shape of the guide hook 6. The guide hook 6 of FIG. 2 may be clipped merely on one side to a guide rail (not shown) or may be guided on both sides, or may be clipped on one side and guided on the other side. The vacuum channel 9 extends centrally through the guide hook 6 and the receiving section 7 and is formed in tube shape in the carrier 2.

In FIG. 3 a front view of the pliable film bag 3—forming the package interior 4—according to aspects of the invention is shown. The film bag 3 of FIG. 3 is printed.

Figure 5:
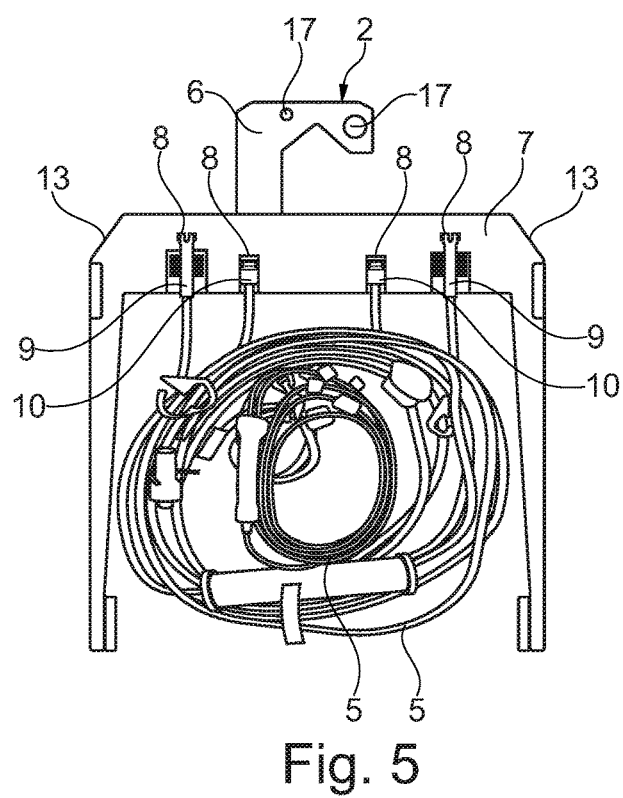
FIG. 5 shows a front view of a carrier of the second embodiment of the packaging device according to aspects of the invention including medical tubes received thereon.

FIG. 4 illustrates a front view of a second embodiment of the sterile package 1 according to aspects of the invention. The sterile package 1 of the second embodiment differs from the first embodiment merely by the design of the carrier 2 so that hereinafter only the differences of the second embodiment from the first embodiment shall be discussed. The carrier 2 of the second embodiment is shown without a film bag 3 in FIG. 5. Although the carrier 2 of the second embodiment has no vacuum channel 11, according to aspects of the invention it is also provided to integrate such vacuum channel into the carrier 2 of the second embodiment. The guide hook 6 of the second embodiment is designed like a hanger hook and has two circular recesses 17. The circular recesses 17 take a circular shape, but they are not intended to be limited to a circular shape and may also be triangular, quadrangular, trapezoidal, oval etc. Thus, analogously to a clothes hanger, the carrier 2 of the second embodiment can be arranged and, respectively, hung/suspended on a guide rail (not shown) via the guide hook 6. In addition or as an alternative, the carrier 2 may also be guided via at least one of the circular recesses 17 provided in the guide hook 6. The guide hook 6 extends perpendicularly outwardly from the receiving section 7 and is centrally arranged. The receiving section 7 is U-shaped so that the receiving section 7 extends in U-shape along the upper edge as well as along the lateral edges of the film bag 3. In this way, the medical tubes 5 accommodated in the package interior 4 are laterally protected.

Figure 6:
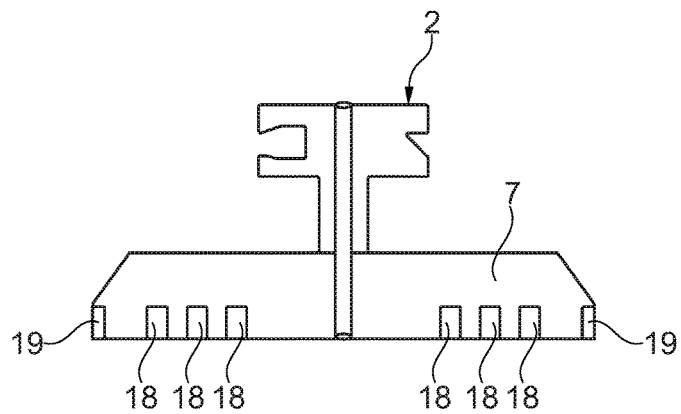
FIG. 6 shows a front view of a possible constructional design of the carrier of the first embodiment.
Figure 7:
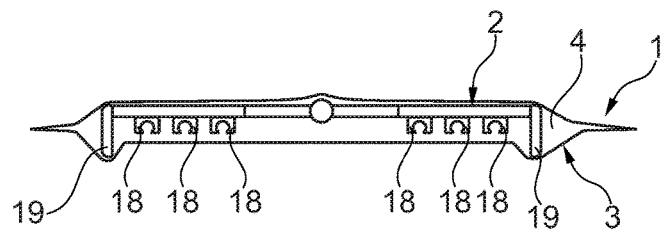
FIG. 7 shows a top view of the carrier of FIG. 6 including the film bag.

FIG. 6 illustrates a front view of a possible constructional design of the carrier 2 of the first embodiment. Here, at the receiving section 7 the carrier 2 includes six connector clips 18 forming the mounts 8 according to aspects of the invention as well as two stacking clips 19. The stacking clips 19 serve for stacking and guiding the entire sterile package 1, each being arranged on the outside of the receiving section 7. In other words, the length of the receiving section 7 approximately corresponds to the distance of the stacking clips 19. FIG. 7 illustrates a top view of the carrier 2 of FIG. 6 including the film bag 3. It is evident that the connector clips 18 are U-shaped/horseshoe-shaped in the top view. The stacking clips 19 span the package interior 4, i.e. the stacking clips 19 form the maximum extension of the receiving section 7 in the depth direction and the film bag 3 is arranged to be, closely adjacent to the stacking clips 19. Applying the film bag 3 to the stacking clips 19 can be even intensified by drawing partial vacuum or vacuum over the vacuum channel 11. Apart from the stacking clips 19, the depth or, respectively, thickness of the receiving section 7 and of the entire carrier 2 is small so that the mass of the sterile package according to aspects of the invention is not unnecessarily increased.

Figure 8:
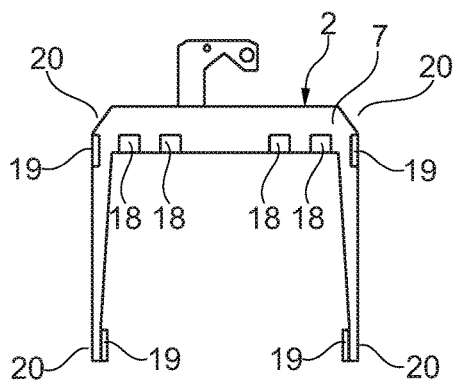
FIG. 8 shows a front view of a possible constructional design of the carrier of the second embodiment.
Figure 9:
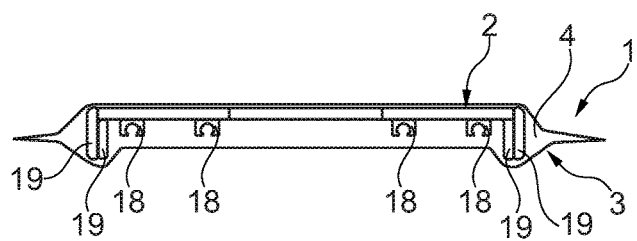
FIG. 9 shows a top view of the carrier of FIG. 8 including the film bag.

In FIG. 8 a front view of a possible constructional design of the carrier 2 of the second embodiment is shown. The receiving section 7 of the carrier 2 in this case comprises four connector clips 18 as well as four stacking clips 19. The stacking clips 19 are provided at corner or end points 20 of the U-shaped receiving section 7 so that the stacking clips 19 are evenly distributed over the sterile package 1 and are arranged at each of the corners of the sterile package 1. By providing four stacking clips 19 in this embodiment stacking and guiding of the entire sterile package 1 may be largely improved as compared to the first embodiment, as now four instead of two stacking points or stacking areas are provided so that a static redundant dimensioning is given. FIG. 9 illustrates a top view of the carrier 2 of FIG. 8 including the film bag 3. In this embodiment, too, the stacking clips 19 span the package interior 4. The film bag 3 also in this case is thus arranged to be closely adjacent to the stacking clips 19.

Figure 10:
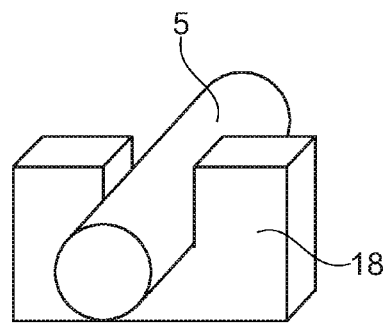
FIG. 10 shows a perspective view of a connector portion according to aspects of the invention.
Figure 11:
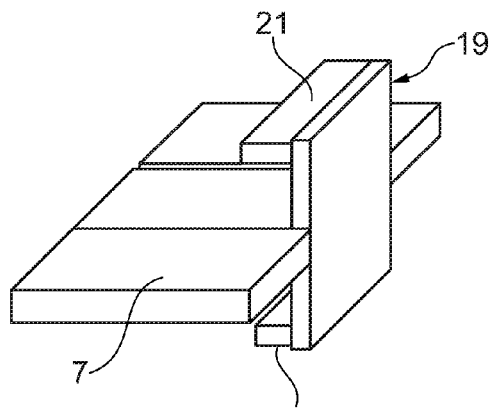
FIG. 11 shows a perspective view of a first embodiment of a stacking portion according to aspects of the invention.
Figure 12:
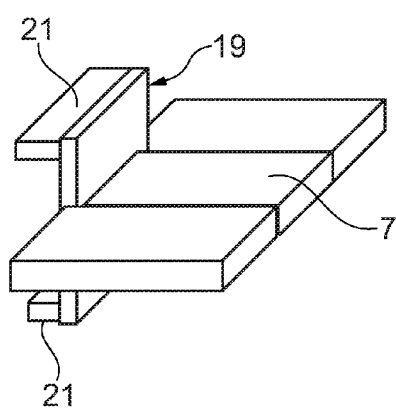
FIG. 12 shows a perspective view of a second embodiment of a stacking portion according to aspects of the invention.

FIG. 10 shows a perspective view of a connector clip 18 according to aspects of the invention. The connector clip 18 is U-shaped so that a section of a medical tube 5 can be arranged thereon by form fit. In FIG. 11 and FIG. 12 perspective views of stacking clips 19 according to aspects of the invention are shown. Each of the stacking clips 19 extends in both directions away from the plane of the receiving section 7 and includes two stacking areas 21 disposed in parallel to the receiving section 7. The stacking areas 21 are arranged to be directed outwardly in FIG. 12 and to be directed inwardly in FIG. 11.

Figure 13:
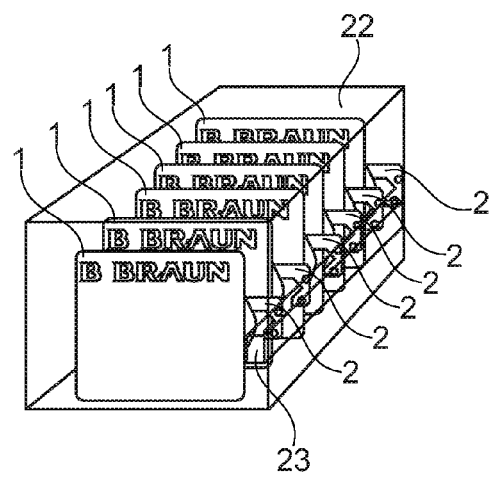
FIG. 13 shows a perspective view of a secondary package according to aspects of the invention comprising packaging devices according to aspects of the invention accommodated therein.
Figure 14:
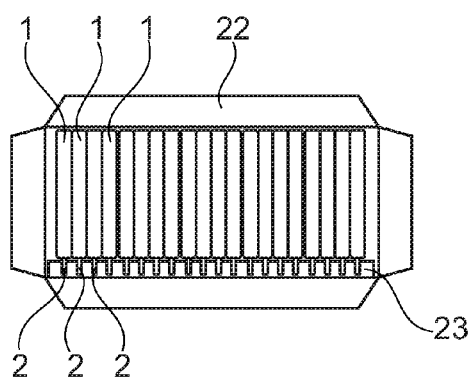
FIG. 14 shows a top view onto a secondary package according to aspects of the invention comprising packaging devices according to aspects of the invention accommodated therein.

FIG. 13 illustrates a perspective view of a receptacle 22 according to aspects of the invention which is capable of receiving a plurality of sterile packages 1. The receptacle 22 has a bottom and four side faces. On one side face a guide rail 23 is provided to which the carriers 2 of the sterile package 1 can be attached. The sterile packages 1 are thus arranged/secured/fixed to the guide rail 23 of the receptacle 22 via the carrier 2 thereof. As is evident from FIG. 13 and FIG. 14, the outer dimensions of the receptacle 22 are chosen such that a width and a height of the receptacle 22 are selected in accordance with the outer dimensions of the sterile package 1. In this way, the sterile packages 1 are achieved to be arranged strung together within the receptacle 22. Thus, on the one hand, the packaging volume of the receptacle is kept small and, on the other hand, it is always immediately visible to a user from outside how many sterile packages 1 are present in the receptacle 22.

The invention claimed is:

1. A packaging device comprising:
   a receiving compartment for medical products to be sterilized or having been sterilized, the receiving compartment sealable in a sterile manner; and
   a carrier configured to at least one of hang, guide, or handle the packaging device, the carrier extending into an interior of the receiving compartment and comprising at least one fitting mount for a section of a medical product to be sterilized or having been sterilized,
   the carrier comprising an outer guiding section configured to at least one of hang, guide, or handle the packaging device,
   the receiving compartment being formed by a film package,
   a bonded connection being formed between the carrier and the film package at an interface where the carrier extends into the receiving compartment, and
   the outer guiding section projecting through the bonded connection and outside of the film package.

2. The packaging device according to claim 1, wherein the carrier further comprises:
   an inner receiving section configured to receive the medical products to be sterilized or having been sterilized, wherein the inner receiving section is arranged inside the receiving compartment.

3. The packaging device according to claim 1, wherein the film package is a film bag having a tab for closing the film bag.

4. The packaging device according to claim 1, wherein the outer guiding section is configured as a guide hook for at least one of orienting, handling, or guiding the packaging device.

5. The packaging device according to claim 4, wherein the guide hook is a hanger hook or T-shaped including two lateral recesses.

6. The packaging device according to claim 1, wherein the at least one fitting mount for the section of the medical product to be sterilized or having been sterilized includes a connector configured to receive, orient, and fix the medical product to be sterilized or having been sterilized in the receiving compartment, wherein the connector comprises a U-shaped recess for form-fittingly securing, clipping, or engaging the medical products to be sterilized or having been sterilized.

7. The packaging device according to claim 1, wherein the at least one fitting mount for the section of the medical product to be sterilized or having been sterilized includes a marking.

8. The packaging device according to claim 7, wherein the at least one fitting mount for the section of the medical product to be sterilized or having been sterilized is adapted as to its shape and/or configuration to the section of the medical product to be sterilized or having been sterilized which is accommodated in said at least one fitting mount.

9. The packaging device according to claim 1, wherein the at least one fitting mount for the section of the medical product to be sterilized or having been sterilized is adapted as to its shape and/or configuration to the section of the medical product to be sterilized or having been sterilized which is accommodated in said at least one fitting mount.

10. The packaging device according to claim 1, wherein in the interior of the receiving compartment the carrier further includes at least two stacking sections spanning the receiving compartment for at least one of stacking or guiding the packaging device.

11. The packaging device according to claim 1, wherein the carrier is U-shaped in the interior of the receiving compartment for laterally protecting the medical products to be sterilized or having been sterilized which are accommodated in the receiving compartment.

12. A secondary packaging in combination with a plurality of packaging devices according to claim 1, wherein the secondary packaging includes a receptacle and a guide rail on which the carriers of the packaging devices are arranged.

13. A packaging device comprising:
    a receiving compartment for medical products to be sterilized or having been sterilized, the receiving compartment sealable in a sterile manner; and
    a carrier configured to at least one of hang, guide, or handle the packaging device, the carrier extending into an interior of the receiving compartment and comprising at least one fitting mount for a section of a medical product to be sterilized or having been sterilized, wherein the carrier includes an evacuating means by which at least a partial vacuum can be produced in the receiving compartment.

14. The packaging device according to claim 13, wherein the evacuating means is a vacuum channel.

* * * * *